United States Patent [19]

Wolf

[11] Patent Number: 5,711,075
[45] Date of Patent: Jan. 27, 1998

[54] UNITARILY FORMED PLASTIC SOFT TISSUE NIPPER

[76] Inventor: Jeffrey A. Wolf, 43 Parkwood Dr., Wayne, N.J. 07470

[21] Appl. No.: 637,849

[22] Filed: Apr. 25, 1996

[51] Int. Cl.[6] .................. B26B 13/18; A61B 17/32
[52] U.S. Cl. .................. 30/28; 30/175; 30/253; 606/174
[58] Field of Search .................. 30/234, 235, 236, 30/244, 253, 329, 331, 28, 175, 186; 606/158, 174, 210

[56] References Cited

U.S. PATENT DOCUMENTS

| D. 250,629 | 12/1978 | Backstrom et al. | 30/253 |
| 2,430,794 | 11/1947 | White | 30/234 |
| 3,659,343 | 5/1972 | Straus | 30/124 |
| 3,906,957 | 9/1975 | Weston | 606/174 |
| 3,972,333 | 8/1976 | Leveen | 606/174 |
| 4,053,979 | 10/1977 | Tuthill et al. | 30/124 |
| 4,092,776 | 6/1978 | Ferguson | 30/253 |
| 4,527,331 | 7/1985 | Lasner et al. | 30/234 |
| 4,669,470 | 6/1987 | Brandfield | 606/174 |
| 5,016,353 | 5/1991 | Iten | 30/124 |
| 5,353,505 | 10/1994 | Okada | 30/253 |
| 5,438,759 | 8/1995 | Dieringer | 30/234 |

FOREIGN PATENT DOCUMENTS 8421 of 1884 United Kingdom ............ 30/234

*Primary Examiner*—Hwei-Siu Payer
*Attorney, Agent, or Firm*—Anthony J. Casella; Gerald E. Hespos; Ludomir A. Budzyn

[57] ABSTRACT

A tissue nipper is provided to permit efficient trimming of tissue, such as cuticles. The nipper is unitarily molded from plastic and includes a base, arms projecting unitarily from the base and cutting blades at the ends of the arms remote from the base. Portions of the arms near the cutting blades are provided with oppositely directed projections that are slidably receivable in grooves of the opposing arm. The projections and grooves guide cutting blades precisely into opposed relationship for efficiently nipping tissue.

8 Claims, 3 Drawing Sheets

UNITARILY FORMED PLASTIC SOFT TISSUE NIPPER

BACKGROUND OF THE INVENTION

1. Field of the Invention

The subject invention relates to a hand held tool for removing soft tissue, such as cuticles at the base of finger nails.

2. Description of the Prior Art

Medical doctors, professional manicurists and self-manicurists frequently utilize hand held tools for cutting soft tissue, such as cuticles. The typical prior art tool for cutting soft tissue is a small metallic scissor or a small metallic nail clipper.

The typical prior art scissor includes two separate blades pivotally connected to one another. Each blade of a typical prior art scissor includes a planar surface orthogonal to the pivot axis. The blades are disposed such that the planar surfaces can slide over one another as the blades are pivoted. Tissue is disposed between the blades such that the plane of the tissue is substantially orthogonal to the planar surfaces of the respective cutting blades. The blades are then pivoted relative to one another and toward the tissue disposed there-between. The blades overlap with one another and cause the tissue therebetween to shear along the planar surfaces of the blades. Thus, scissors of this type often are referred to as shears.

Shears require space on either side of the tissue being cut for placement of the blade prior to shearing. The amount of space required is a function of the width of each blade and the length of each blade from the pivot point. Cuticles necessarily do not provide significant room on either side for efficient operation of most shears. As a result, shears used for cuticles have short and very pointed blades. Handle portions of such shears must be sufficiently large for digital manipulation by the doctor or manicurist. As a result, these shears have a very significant mechanical advantage applied to the blades by the handles. Hence, a small force on the handles generates a large force by the blades.

These prior art shears are well suited for many tasks but present problems for cuticle removal and other soft tissue cutting. In particular, the sharply pointed blade can lead to accidental puncture wounds. Additionally, the very significant mechanical advantage attributable to the long handles and short blades can lead to the accidental and painful cutting of live tissue. These relative dimensions of the handle and cutting blade portions also make it difficult for the person using these shears to have an efficient feel for the work being performed.

The prior art metallic shears present other problems for the doctor or professional manicurist. In particular, good quality metallic shears are too expensive to be disposable after each use. Consequently, doctors and professional manicurists will use shears for several different patients. Doctors typically have equipment for adequately sterilizing shears between adjacent uses. Professional manicurists, however, generally do not have sterilization equipment. At best, a professional manicurist may deposit the working end of a set of shears into a solution that the manicurist hopes will prevent the spread of communicable diseases. Such solutions often are ineffective. Furthermore, the consumer cannot be certain that an attempt to sterilize tools will have been attempted. Similar problems exist within each household where shears for trimming cuticles may be used by several individuals with no attempt to sterilize the shears between such uses. Household cuticle shears often are stored in a warm moist bathroom that breeds bacteria.

Many soft tissue cuts, such as cuticle trimming, requires precise cutting to be carried out within a very small area. An imprecise cut can be painful and lead to an open bleeding wound. Observation of the area being cut often is impeded by the opaque metallic blades and/or pivot region of the shears.

The relatively high cost of most prior art shears is partly attributable to the relatively high cost of the metal used to make the shears. Furthermore, most prior art shears are formed from two members that must be separately manufactured and then assembled. The need for separate members and their subsequent assembly adds to the cost of the product.

The prior art also includes shears where the handles are disposed between cutting blades and the pivot point. Some such shears are formed from unitary pieces of metal bent into a U-shape. The metal is selected to exhibit resilient spring characteristics near the apex of the U. The ends of the U remote from the apex include the cutting blades. Portions of the arms between the apex and the cutting blade may include complex assemblies of latches and guides to control the range of movements of the cutting blades. Examples of such shears are shown, for example, in U.S. Pat. Nos. 2,430,794, 4,527,331, and 5,353,505. The prior art also includes such shears where the handles and the apex are unitarily molded from plastic material. Metallic cutting blades are then fixed to ends of the plastic handles remote from the apex of the U. Examples of prior art shears of this general type are shown in U.S. Pat. Nos. 3,972,333 and 4,092,776.

Some prior art cutting tools do not rely upon the overlapping shearing action of the blades. For example, nippers include sharply beveled blades with cutting edges that are moved into directly opposite relationship with one another. Some prior art nippers include two metallic members pivoted at a central location in much the same manner as the above-described shears. Manual forces on the handles urge the cutting blades towards one another, and into opposite respective sides of the material being cut. Sufficient movement of the blades will cause the material to be cut along the line coincident with the cutting edges of the prior art nipper. The typical prior art nipper for toe nails or finger nails has large handles and small cutting blades to provide a significant mechanical advantage. For the reasons explained above, this can result in very little tactile sensation by the person manipulating the nipper. Thus, a painful cutting of live tissue can unintentionally be completed before the person using the nipper can react. These prior art metallic nippers also suffer the above-described deficiencies of shears in that they are costly and provide poor visibility of the work area.

Some prior art nippers that are intended as nail cutters include two elongate elements connected at one end and having cutting edges generally transverse to the longitudinal axis of each member. A lever is used to urge one cutting blade toward the other to complete the cutting. The lever may be rotatable between a first position where the nail clipper is well suited for storage and a second position where the lever projects outwardly from the elongate element and into a position where movement of the lever urges the cutting blades towards one another. This prior art nipper offers some conveniences for cutting nails, but is not well suited for trimming cuticles or other soft tissue cutting.

Significant room for improvement exists with respect to soft tissue nippers, and particularly nippers suitable for trimming cuticles.

3

Accordingly, it is an object of the subject invention to provide improved soft tissue nippers.

It is another object of the subject invention to provide soft tissue nippers that are inexpensive.

A further object of the subject invention is to provide soft tissue nippers that afford good tactile sensation for the person using the nippers.

Still another object of the subject invention is to provide soft tissue nippers that afford good visibility of the tissue being cut.

It is still a further object of the subject invention to provide an inexpensive tool that enables the performance of several different functions associated with manicures or pedicures.

SUMMARY OF THE INVENTION

The subject invention is directed to soft tissue nippers having a base, a pair of arms unitarily projecting from the base and a pair of blades at ends of the respective arms remote from the base. The nippers may be of unitary construction, and preferably are unitarily molded from a plastic material. An acrylic material has proved to provide the desired strength and resiliency for the arms and base while simultaneously providing desirable sharpness characteristics for the blades. The plastic material of the subject nippers may be transparent to provide acceptable viewing of the area being cut.

As noted above, nippers require the blades to be urged into abutting edge-to-edge contact. Most prior art nippers achieve this functional requirement by providing two separate members that are pivotally connected to one another at locations close to the cutting edges. This prior art construction virtually precludes the unitarily formed nippers. The nippers of the subject invention have blades disposed at locations spaced from the base by a distance equal to the length of the respective arms. The arms, necessarily, must be sufficiently long for efficiently accommodating the hand of the user. In view of this distance between the base and the nipper blades, a potential for blade misalignment during cutting exists. This potential is overcome by guides unitarily incorporated into the arms of the nipper of the subject invention. More particularly, at least a first of the two arms is provided with a guiding projection, and at least a second of the two arms is provided with a guide groove into which the projection is slidably received. The interengagement of the projection and the groove ensures that the cutting edges of the respective blades will move into abutting contact with one another. Preferably, each arm includes both a projection and a recess into which the opposed projection is slidably received. The projections and the recesses may be unitarily molded as part of the subject nipper.

Each projection of the nipper may include a locking tang for snapped engagement with a corresponding rib on the opposed groove. Engagement of the locking tang and the rib prevent excessive extension of the arms away from one another. The locking tang and the rib are dimensioned and disposed to require the arms to be biased toward one another for engagement. The resiliency of the material of the nipper will therefore urge the arms away from one another and into a slightly opened position.

4

Figure 2:
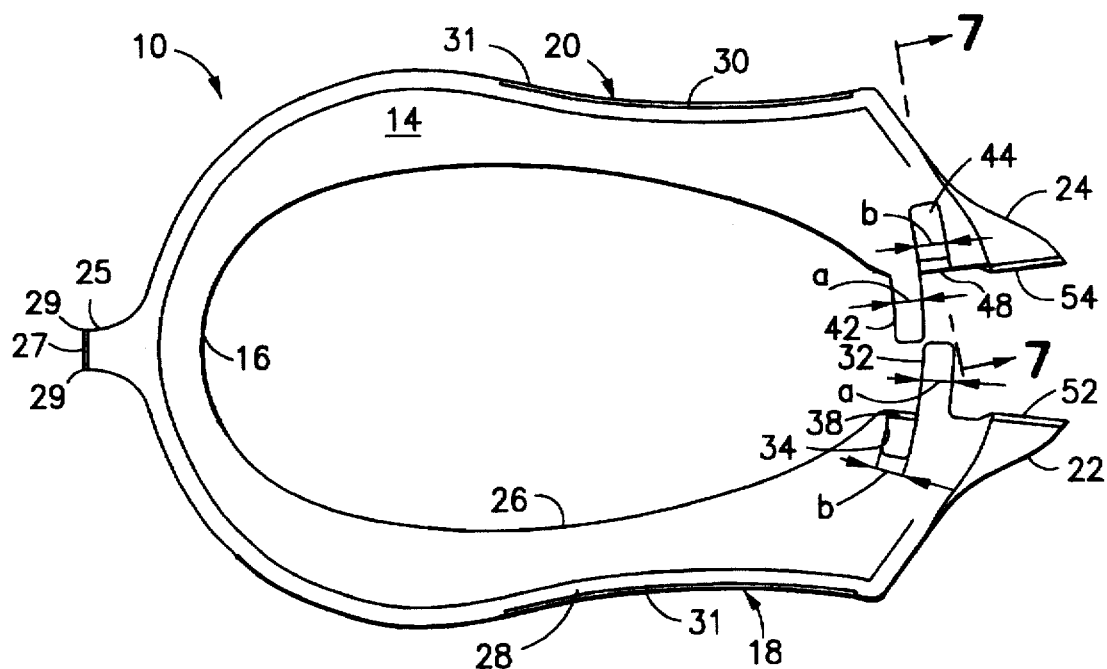
FIG. 2 is a bottom plan view thereof.
Figure 3:
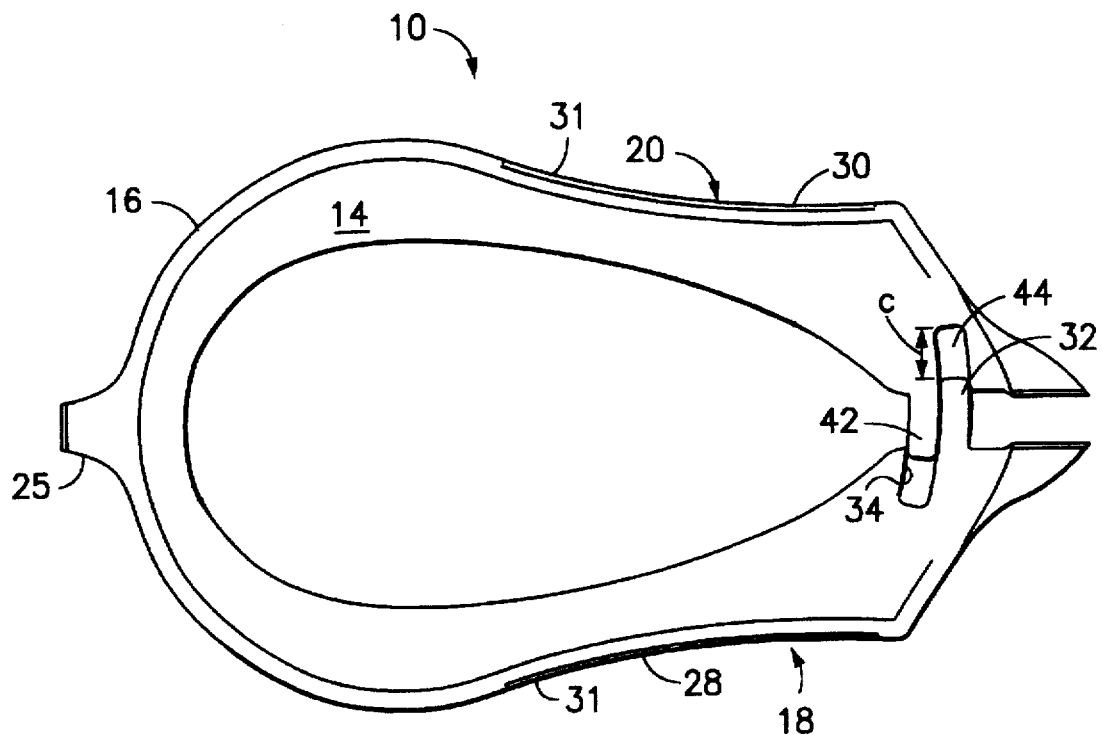

FIG. 3 is a bottom plan view similar to FIG. 2, but showing the nippers in a biased ready to use condition.

Figure 4:
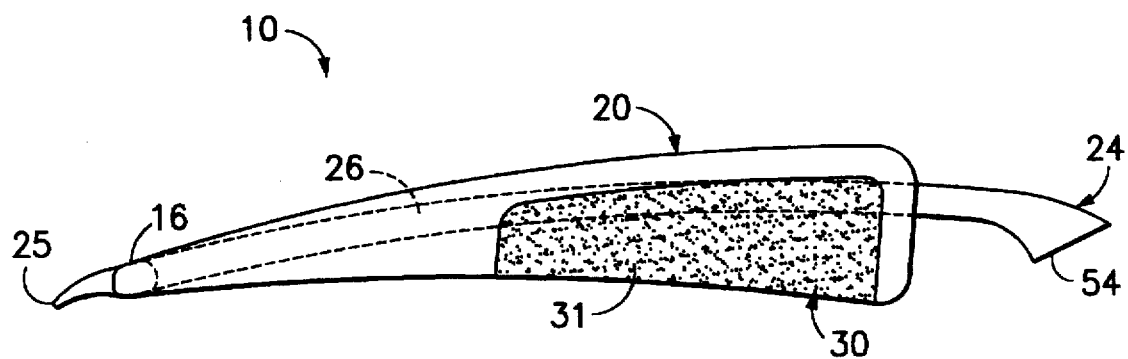

FIG. 4 is a side elevational view of the nippers.

Figure 1:
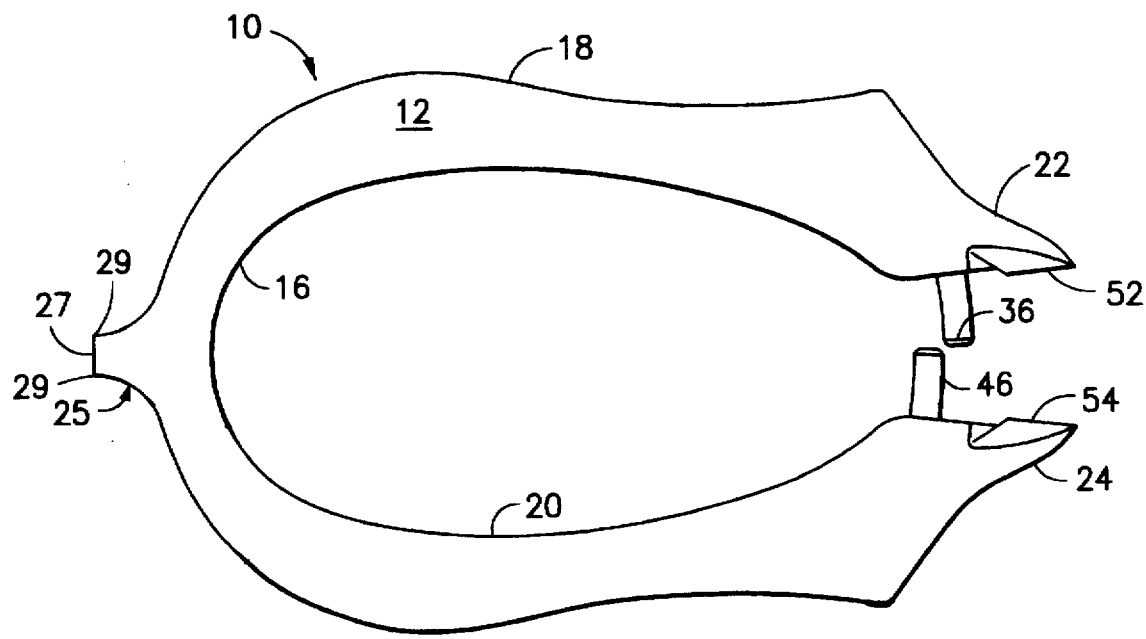
FIG. 1 is a top plan view of a tissue nipper in accordance with the subject invention in an unbiased condition.
Figure 5:
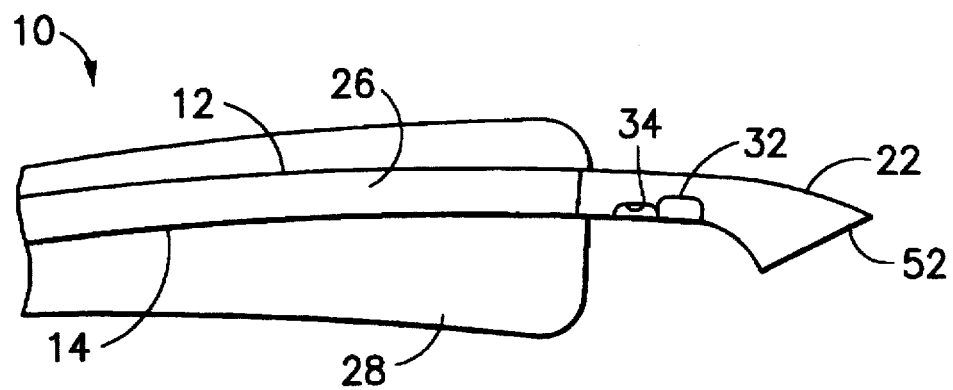

FIG. 5 is a cross-sectional view taken along line 5—5 in FIG. 1.

Figure 6:
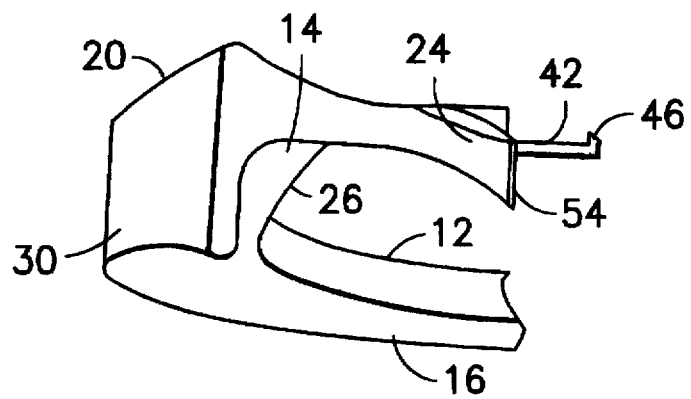

FIG. 6 is a partial front view, as taken from the left side of FIG. 2.

Figure 7:
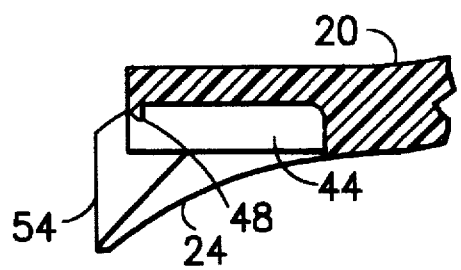

FIG. 7 is a cross-sectional view taken along line 7—7 in FIG. 2.

DETAILED DESCRIPTION OF THE PREFERRED EMBODIMENT

A tissue nipper in accordance with the subject invention is identified generally by the numeral 10 in FIGS. 1–7. The nipper 10 is unitarily molded from a transparent acrylic, and hence permits visual observation of the area being cut. The nipper 10 includes a top surface 12, as shown most clearly in FIG. 1, and an opposed bottom surface 14, as shown most clearly in FIGS. 2 and 3.

The nipper 10 is molded to define a base region 16, first and second arms 18 and 20 and first and second blades 22 and 24 at end regions of the first and second arms 18 and 20 remote from the base 16. A scraper 25 projects unitarily from the base 16 in a direction opposite the arms 18 and 20. The scrapper 25 includes a convex edge 27 for pushing cuticles and corners 29 for scraping under nails.

The arms and base are formed to define a continuous support wall 26 that is arched slightly convexly upwardly between the base and the cutting blades as shown in FIGS. 4 and 5. The arms 18 and 20 further include finger flanges 28 and 30 projecting downwardly from the support wall 26 to locations below the cutting blades 22 and 24 respectively.

With reference to FIGS. 2 and 3, the finger flanges 28 and 30 have outwardly facing concave surfaces dimensioned and configured for easy and convenient digital manipulation. Outer surface regions of the finger flanges 28 and 30 further are provided with sections of emery 31 adhered thereon. The emery 31 functions to provide a secure slip-free grip, and further enables use of the emery 31 as part of manicuring services.

Inwardly directed forces on the finger flanges 28 and 30 will deflect the arms 18 and 20 about the base 16 such that the cutting blades 22 and 24 are urged toward one another. Additionally, in view of the lower disposition of the finger flanges 28 and 30, inwardly directed forces on the finger flanges 28 and 30 will generate forces that urge the cutting blades 22 and 24 upwardly. These upward forces are controlled and used beneficially to align the blades as explained below.

The bottom surface 14 of the first arm 18 in proximity to the cutting blade 22 is provided with a first projection 32 and a first groove 34. The first projection 32 extends arcuately from the first arm 18 toward the second arm 20 to define a section of an arc through which the first projection 32 will move as the first arm 18 is deflected relative to the base 16. As shown in FIG. 2, the first projection 32 defines a radial width "a". An upwardly facing tang 36 is defined on a portion of the first projection 32 nearest the second arm 20. The first groove 34 extends into the bottom surface 14 of the first arm 18 at a location radially inwardly from the first projection 32. The groove 34 also is generated arcuately about the same center as the first projection 32. Portions of the first groove 34 nearest the second arm 20 define a downwardly projecting lip 38 as shown most clearly in FIG. 2. The radial width of the first groove 34 is indicated by dimension "b" in FIG. 2 and is slightly greater than the radial width "a" of the projection 32.

The second arm 20 includes a second projection 42 and a second groove 44 which are substantially similar to the first projection 32 and first groove 34 on the first arm 18. However, the second groove 44 is disposed between the second projection 42 and the second cutting blade 24. The second projection 42 has a width "a" substantially identical to the width "a" of the first projection 32 and less than the width "b" of the first groove 34. Additionally, the second projection 42 includes an upwardly extending tang 46 as shown most clearly in FIG. 1. The second groove 44 is characterized by a downwardly projecting lip 48 at locations thereon nearest the first arm 18. The second groove 44 is formed to define a width "b" which exceeds the width "a" of the first projection 32.

As shown in FIGS. 2 and 3, the first and second projections 32 and 42 are disposed and dimensioned to be slidably received within the second and first grooves 44 and 34 respectively. Additionally, the tangs 36 and 46 of the projections 32 and 42 respectively are disposed and dimensioned to lockingly engage the lips 48 and 38 in the grooves 44 and 34 respectively. With this construction, the first projection 32 can be snapped into the second groove 44, while the second projection 42 can be snapped into the first groove 34. This snapped engagement of the projections 332 and 42 in the grooves 44 and 34 respectively biases the arms 18 and 20 into the positions shown in FIG. 3. As shown in FIG. 3, the distance "c" between ends of the respective projections 32 and 42 and ends of the associated grooves 44 and 34 is greater than the distance "d" between the cutting blades 22 and 24. Thus, the projections 32 and 42 and the associated grooves 44 and 34 permit the arms 18 and 20 to be biased toward one another a sufficient distance for the cutting blades 22 and 24 to contact one another.

The interengagement of the projections 32 and 42 and the grooves 34 and 44 achieve several significant advantages. First, the arms 18 and 20 are prevented from being biased too far apart in a manner that could break the arms 18 and 20 near the base 16 or that could push the arms beyond their elastic limit. Thus, the cutting blades 22 and 24 are maintained in closely spaced relationship to one another. Additionally, the interengagement of the projections 32 and 42 with the corresponding grooves 44 and 34 guide the movement of the cutting blades 22 efficiently toward one another for cutting tissue. In particular, with reference to FIG. 4, the finger flanges 28 and 30 are disposed below the bottom surface of the support wall 26, and hence below the interengaged projections 32 and 42 and grooves 44 and 34. Thus, digital forces exerted on the finger flanges 28 and 30 urge the projections 32 and 42 upwardly and into the corresponding grooves 44 and 34. In this manner, the cutting blades are moved toward one another along a precisely defined path which ensures that the blades will move into edge-to-edge abutment rather than sliding into an ineffective overlapping condition.

Cutting blades 22 and 24 project outwardly and downwardly from portions of the support wall 26 furthest from the base 16. More particularly, the cutting blades 22 and 24 terminate in sharp edges 52 and 54 respectively. The edges define an angle of approximately 30 degrees to the support wall 26 as shown most clearly in FIG. 5. Additionally, the blades are configured to extend into a point from top to bottom as shown in FIGS. 4 and 5 and from side-to-side as shown in FIGS. 1–3. The pointed configuration facilitates access and targeting of small areas of tissue to be nipped.

The nippers 10 can be used in conventional fashion by merely positioning areas of tissue to be trimmed between the edges 52 and 54 of the blades 22 and 24 respectively. Digitally directed forces are then exerted on the finger flanges 28 and 30 to deflect the arms 18 and 20 toward one another and about locations in proximity to the base 16. The position of the finger flanges 28 and 30 between the points of deflection of the arms 18 and 20 and the cutting blades 22 and 24 ensures that no excessive mechanical advantage is provided for the person using the cutter. Thus, the person manipulating the nipper 10 has a very good tactile sensation throughout the cutting procedure and is less likely to accidentally cut live tissue that was not targeted. The targeting of tissue to be cut is facilitated by the transparent nature of the acrylic material from which the nipper 10 is molded. In particular, the nipper necessarily is disposed between the eyes of the person gripping the nipper and tissue areas to be cut. However, the target areas can be readily viewed through the transparent acrylic in proximity to the cutting edges 22 and 24. Cutting can be carried out efficiently by merely urging the finger flanges 28 and 30 toward one another. The position of the finger flanges 28 and 30 below the support walls 26 substantially ensures that the projections 32 and 42 will be slidably retained within the grooves 44 and 34. Hence, the cutting edges 52 and 54 will be urged precisely into opposing relationship with one another for efficiently cutting through the tissue.

Manicuring carried out with the nippers is facilitated by the provision of emery on outwardly facing regions of the finger flanges 28 and 30. The respective patches of emery may be of different respective roughnesses for accommodating different nail filing needs. Additionally, the emery may wrap around bottom portions of the finger flanges 28 and 30 to further enhance the filing options. The scraper 25 projecting from the base 16 and away from the arms 18 and 20 may be used to scrape under nails as part of the manicuring process.

While the invention has been described with respect to a preferred embodiment, it is apparent that changes can be made without departing from the scope of the invention.

I claim:

1. A tissue nipper unitarily molded from a plastic material and comprising a base, first and second arms projecting from said base and cutting blades at ends of said arms remote from said base, each said cutting blade having a cutting edge, said arms each having a support wall with opposed top and bottom surfaces, guides projecting from each said arm at locations spaced from the base, the guide of each said arm being slidably engaged against the bottom surface of the support wall of the other of said arms, finger flanges projecting downwardly from said support wall for receiving digital pressure thereon, said digital pressure on said finger flanges urging said guides against the bottom surface of the support wall of the opposed arm and resiliently deflecting said arms toward one another into a position where said cutting edges are in abutting edge-to-edge contact with one another.

2. The tissue nipper of claim 1 further comprising emery disposed on the finger flanges for facilitating gripping of the tissue nipper and for enabling filing of nails.

3. The tissue nipper of claim 1 wherein said projection includes an end having a detent formed thereon, said groove being formed with a lip engagable with said detent for retaining said projection in said groove and for holding said arms in a biased position.

4. The tissue nipper of claim 1 further comprising a scraper projecting unitarily from said base and in a direction opposite from said arms, said scraper having a convex end for pushing cuticles, said scraper further having at least one corner for scraping under nails.

5. A tissue nipper unitarily molded from plastic and comprising a base, first and second arms projecting from said base and cutting blades at ends of said arms remote from said base, each said cutting blade having a cutting edge, said arms each comprising a finger engagement surface disposed intermediate said base and said cutting blades and being configured for receiving digital pressure thereon, said arms being resiliently deflectable in response to said digital pressure on said finger engagement surfaces from a condition where said cutting edges are in spaced relationship into a position where said cutting edges are in abutting edge-to-edge contact with one another, said finger engagement surfaces having emery disposed thereon for enabling filing of nails, portions of each said arm in proximity to the cutting blade thereof having a guide projection slidably engaged with the other of said arms for guiding the cutting edges of said cutting blades into abutting engagement with one another in response to said digital pressure on the finger engagement surfaces.

6. A tissue nipper unitarily molded from plastic and comprising a base, first and second arms projecting from said base and cutting blades at ends of said arms remote from said base, each said cutting blade having a cutting edge, said arms each comprising a finger engagement surface disposed intermediate said base and said cutting blades and being configured for receiving digital pressure thereon, said arms being resiliently deflectable in response to said digital pressure on said finger engagement surfaces from a condition where said cutting edges are in spaced relationship into a position where said cutting edges are in abutting edge-to-edge contact with one another, portions of each said arm in proximity to said cutting blade thereof having a guide projection slidably engaged with the other of said arms for guiding the cutting edges of said cutting blades into abutting engagement with one another in response to said digital pressure on the finger engagement surfaces, a scrapper projecting unitarily from said base and in a direction opposite from said arms, said scraper having an end for pushing cuticles and having at least one corner for scrapping under nails.

7. A tissue nipper unitarily molded from plastic and comprising a base, first and second arms projecting from said base and cutting blades at ends of said arms remote from said base, said arms each having opposed top and bottom surfaces, said cutting blades having cutting edges angled downwardly and toward said base at acute angles from said top surfaces of said arms, said arms being resiliently deflectable from a condition where said cutting edges are in spaced relationship to one another into a position where said cutting edges are in abutting edge-to-edge contact with one another, portions of each said arm in proximity to said cutting blade thereof having a guide projection slidably engaged with the other of said arms for guiding the cutting edges of said cutting blades into abutting edge-to-edge engagement with one another in response to deflection of the arms towards one another.

8. The tissue nipper of claim 7, wherein the acute angle is approximately 30°.

* * * * *